US008823529B2

(12) United States Patent
Reed, Jr.

(10) Patent No.: US 8,823,529 B2
(45) Date of Patent: Sep. 2, 2014

(54) PATIENT MOVEMENT MONITORING SYSTEM

(75) Inventor: Donald N. Reed, Jr., Fort Wayne, IN (US)

(73) Assignee: DRS Medical Devices, LLC, Fort Wayne, IN (US)

( * ) Notice: Subject to any disclaimer, the term of this patent is extended or adjusted under 35 U.S.C. 154(b) by 98 days.

(21) Appl. No.: 13/565,428

(22) Filed: Aug. 2, 2012

(65) Prior Publication Data
US 2014/0035749 A1 Feb. 6, 2014

(51) Int. Cl.
G08B 23/00 (2006.01)
G08B 21/22 (2006.01)

(52) U.S. Cl.
CPC ..................... G08B 21/22 (2013.01)
USPC .............. 340/573.4; 340/539.11; 340/539.23; 340/540; 340/541; 340/542; 340/521

(58) Field of Classification Search
CPC ....................................... G08B 21/22
USPC ............ 340/573.4, 539.11, 539.23, 540, 541, 340/542, 521
See application file for complete search history.

(56) References Cited

U.S. PATENT DOCUMENTS

| 4,196,425 | A | 4/1980 | Williams, Jr. et al. |
| 4,638,307 | A | 1/1987 | Swartout |
| 4,716,402 | A | 12/1987 | Francis |
| 4,843,374 | A | 6/1989 | Sansky |
| 4,947,152 | A | 8/1990 | Hodges |
| 4,951,032 | A | 8/1990 | Langsam |
| 5,371,489 | A | 12/1994 | Carroll et al. |
| 5,434,556 | A | 7/1995 | Donohoo |
| 5,471,198 | A | 11/1995 | Newham |
| 5,600,305 | A | 2/1997 | Stafford et al. |
| 5,633,627 | A | 5/1997 | Newham |
| 5,640,145 | A | 6/1997 | Newham |
| 5,654,694 | A | 8/1997 | Newham |

(Continued)

FOREIGN PATENT DOCUMENTS

WO WO 01/95280 A1 12/2001
WO WO 2009/029996 A1 3/2009

OTHER PUBLICATIONS

Jasco Products Company LLC, 45129 GE Wireless Alarm System Control Center User's Manual Choice Alert, 20 pages, Nov. 2, 2007.

(Continued)

Primary Examiner — Tai T Nguyen
(74) Attorney, Agent, or Firm — Bose McKinney & Evans LLP

(57) ABSTRACT

A patient monitoring system having a motion detection unit with a sensor and a control unit having control circuitry and at least one light. Wiring extends between the two units and couples a motion sensor with the control circuitry. A door sensor is coupled with the control circuitry. The light is illuminated to provide a silent alarm when motion is detected and the door is closed. Also disclosed is a method of installation that includes attaching a motion detector unit and the control unit to wall surfaces on opposite sides of the door and extending wiring through the doorway to operably couple the two units. The motion sensor may be installed to define a detection zone having a lower boundary which is at least about 18 inches above a patient support surface.

20 Claims, 5 Drawing Sheets

(56) References Cited

U.S. PATENT DOCUMENTS

| | | | |
|---|---|---|---|
| 6,111,509 A | 8/2000 | Holmes | |
| 6,204,767 B1 | 3/2001 | Sparks | |
| 6,441,742 B1 | 8/2002 | Lovely et al. | |
| 6,741,163 B1 | 5/2004 | Roberts | |
| 6,788,206 B1 | 9/2004 | Edwards | |
| 6,812,836 B2 | 11/2004 | Soloway et al. | |
| 6,950,017 B2 * | 9/2005 | Smith | 340/521 |
| 7,012,533 B2 * | 3/2006 | Younse | 340/573.1 |
| 7,132,941 B2 * | 11/2006 | Sherlock | 340/539.26 |
| 7,151,457 B2 | 12/2006 | Riley et al. | |
| 7,268,682 B2 | 9/2007 | Bialecki, Jr. et al. | |
| 7,443,304 B2 | 10/2008 | Rowe et al. | |
| 7,733,228 B2 * | 6/2010 | Lee et al. | 340/572.1 |
| 7,764,167 B2 * | 7/2010 | Reeves et al. | 340/426.22 |
| 7,916,018 B2 | 3/2011 | Eskildsen et al. | |
| 7,920,061 B2 | 4/2011 | Klein et al. | |
| 7,987,069 B2 | 7/2011 | Rodgers et al. | |
| 8,655,547 B1 * | 2/2014 | Steele | 701/36 |
| 2007/0040692 A1 | 2/2007 | Smith et al. | |
| 2008/0204258 A1 | 8/2008 | Dayton et al. | |
| 2010/0033331 A1 | 2/2010 | Bautovich | |

OTHER PUBLICATIONS

Jasco Products Company LLC, 45132 GE Wireless Alarm System Motion Sensor User's Manual Choice Alert, 16 pages, Jan. 18, 2008.
Jasco Products Company LLC, 45137 GE Wireless Alarm System Silent Alert User's Manual Choice Alert, 12 pages, Jan. 9, 2008.
Posey Company, Posey KeepSafe Alarm, 2 pages, Arcadia, CA, 2012.
Posey Company, Posey KeepSafe Essential Door Guard Alarm/Do Not Enter Banner Alarm, 2 pages, Arcadia, CA, 2012.
Posey Company, Sitter Elite Instruction Manual, 40 pages, Arcadia, CA, 2011.
Posey Company, Posey Door Guard/Do Not Enter Alarm, 2 pages, Arcadia, CA, 2010.

* cited by examiner

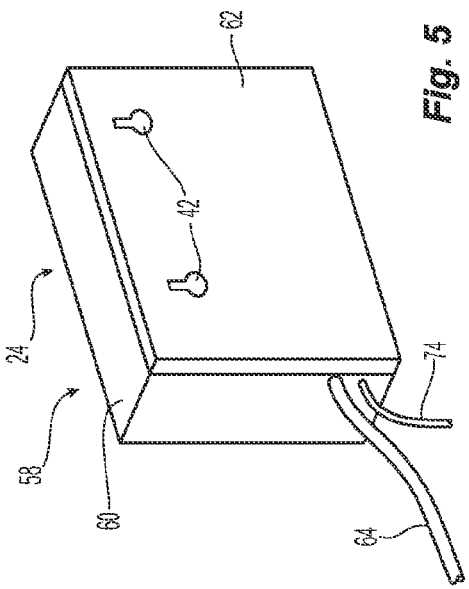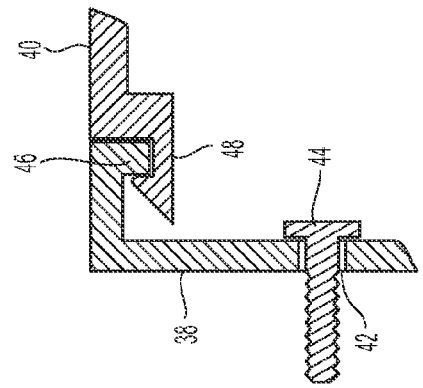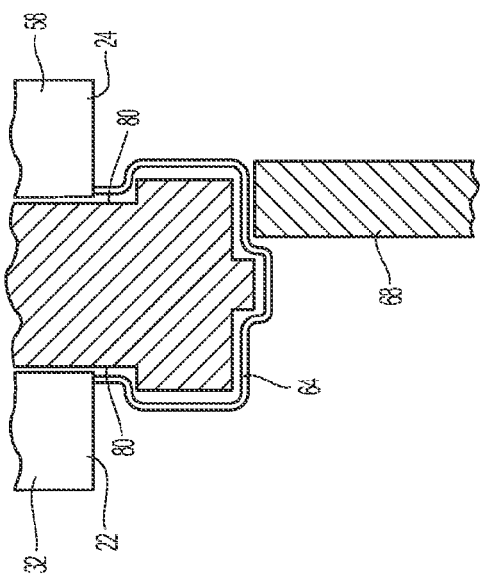

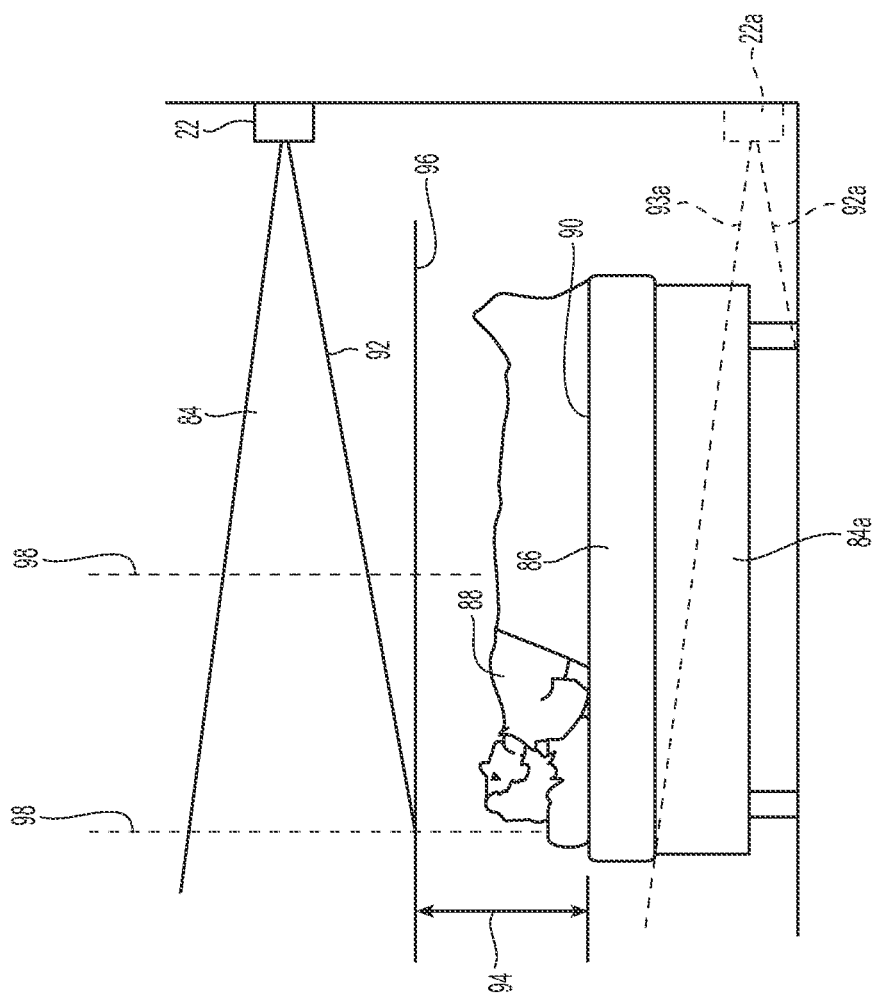

PATIENT MOVEMENT MONITORING SYSTEM

BACKGROUND OF THE INVENTION

1. Field of the Invention

The present invention relates to systems which monitor patient movement and, more particularly, to systems which can be used to alert a caregiver when a patient is ambulatory.

2. Description of the Related Art

Care facilities, such as hospitals, long-term care facilities, and elderly care facilities, have many patients that present a "fall-risk." For example, some elderly patients are still ambulatory but are unstable on their feet. If such patients fall from a standing position or while getting out of bed they can break bones, e.g., a hip or rib, or otherwise significantly injure themselves. Such patients do not always follow the instructions of caregivers and may attempt to get out of their bed or walk unassisted despite contrary health-care instructions.

A variety of monitoring systems are known for such "fall-risk" patients. For example, pads which are capable of detecting weight may be placed on the bed and generate an alarm signal when a weight is removed from the pad, e.g., when a patient moves off of the pad. Such pads, however, have not always proven to be effective for lighter weight patients. Some such pads have also been known to have only a short useful life before becoming worn and unreliable.

It is also known to use motion detectors to determine when a fall-risk patient has exited a bed. Many of the systems employing motion detectors can be relatively expensive and many care facilities find the deployment of such systems to be cost-prohibitive.

While known patient monitors can effectively alert caregivers when a fall-risk patient is exiting a bed, further improvements in such monitoring systems are desirable.

SUMMARY OF THE INVENTION

The present invention provides a cost-effective patient monitoring system that can be used to alert a caregiver when a patient is exiting a bed. Systems in accordance with the present invention are also adapted for use in a care facility with a "closed-door" policy to limit noise levels.

Hospitals and other care facilities typically include a significant amount of medical equipment. Many of the individual pieces of medical equipment include audible alarms and generate other forms of audible noise during operation and such care facilities have become noisier in recent years as the amount of installed equipment has grown. As a result, many care facilities are implementing "closed door" policies under which it is customary practice to keep the door of individual patient rooms closed unless a caregiver is present in the room with the patient. By keeping the doors of each of the patient rooms closed, not only is the patient within the room shielded from much of the noise generated outside the room, but the surrounding area is also shielded from the noise generated within the room. Patient monitoring systems in accordance with the present invention are well-adapted for use in a care facility having such a closed door policy.

The invention comprises, in one form thereof, a patient monitoring system for use proximate a doorway with a door. The system includes a motion detection unit having a motion detection sensor and a first housing supporting the motion detection sensor. A control unit includes control circuitry, at least one light operably coupled with the control circuitry and a second housing which supports the control circuitry and the light. The light indicates one of an alarm condition and a non-alarm condition by selective illumination of the light. Wiring extends between the first housing and the second housing and operably couples the motion detection sensor with the control circuitry wherein the control circuitry receives signals from the motion detection sensor. The system also includes a door sensor assembly that is securable proximate a door. The door sensor assembly is operably coupled with the control circuitry thereby communicating the open/closed status of the door to the control circuitry. The control circuitry is configured to place the light in the alarm condition when the motion detector senses movement and the door sensor assembly detects that the door is closed.

The invention comprises, in another form thereof, a method of installing a patient monitoring system. The method includes attaching a first housing to a first wall surface on a first side of a door opening wherein the first housing supports a motion detection sensor and attaching a second housing to a second wall surface on an opposite side of the door opening wherein the second housing supports control circuitry and at least one light operably coupled with the control circuitry. The light indicates one of an alarm condition and a non-alarm condition by selective illumination of the light. The motion detection sensor is operably coupled with the control circuitry by extending wiring therebetween with the wiring extending through the door opening. A door sensor assembly is mounted proximate the door opening and operably coupled to the control circuitry. The method also includes detecting whether the door is open or closed with the door sensor assembly and placing the light in the alarm condition when the motion detector senses movement and the door sensor assembly detects that the door is closed.

In some embodiments, all of the electrical communicating components of the system are mounted exterior to the first and second wall surfaces.

In still other embodiments, the first housing is positioned on the first wall surface wherein the motion detection sensor defines a detection zone having a lower boundary which is at least about 18 inches above the support surface.

BRIEF DESCRIPTION OF THE DRAWINGS

The above mentioned and other features of this invention, and the manner of attaining them, will become more apparent and the invention itself will be better understood by reference to the following description of an embodiment of the invention taken in conjunction with the accompanying drawings, wherein:

FIG. 4 is a rear perspective view of a motion detection unit.

FIG. 5 is a rear perspective view of a control unit.

FIG. 6 is a schematic cross sectional view through a door jamb.

FIG. 7 is a partial view of a housing.

FIG. 8 is a view of a hospital room showing a detection zone.

Figure 1:
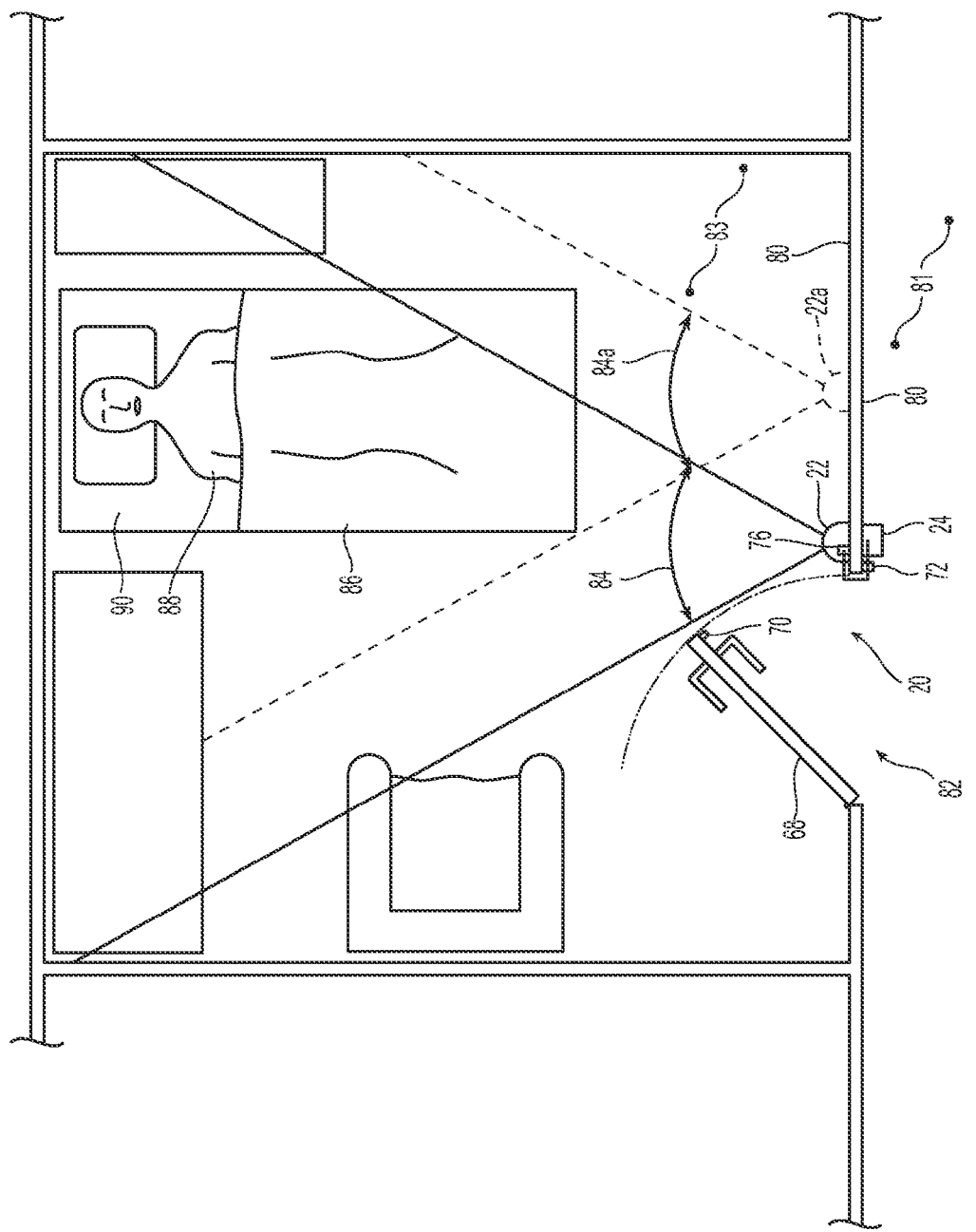
FIG. 1 is a schematic plan view of a hospital room with an installed patient monitoring system.
Figure 2:
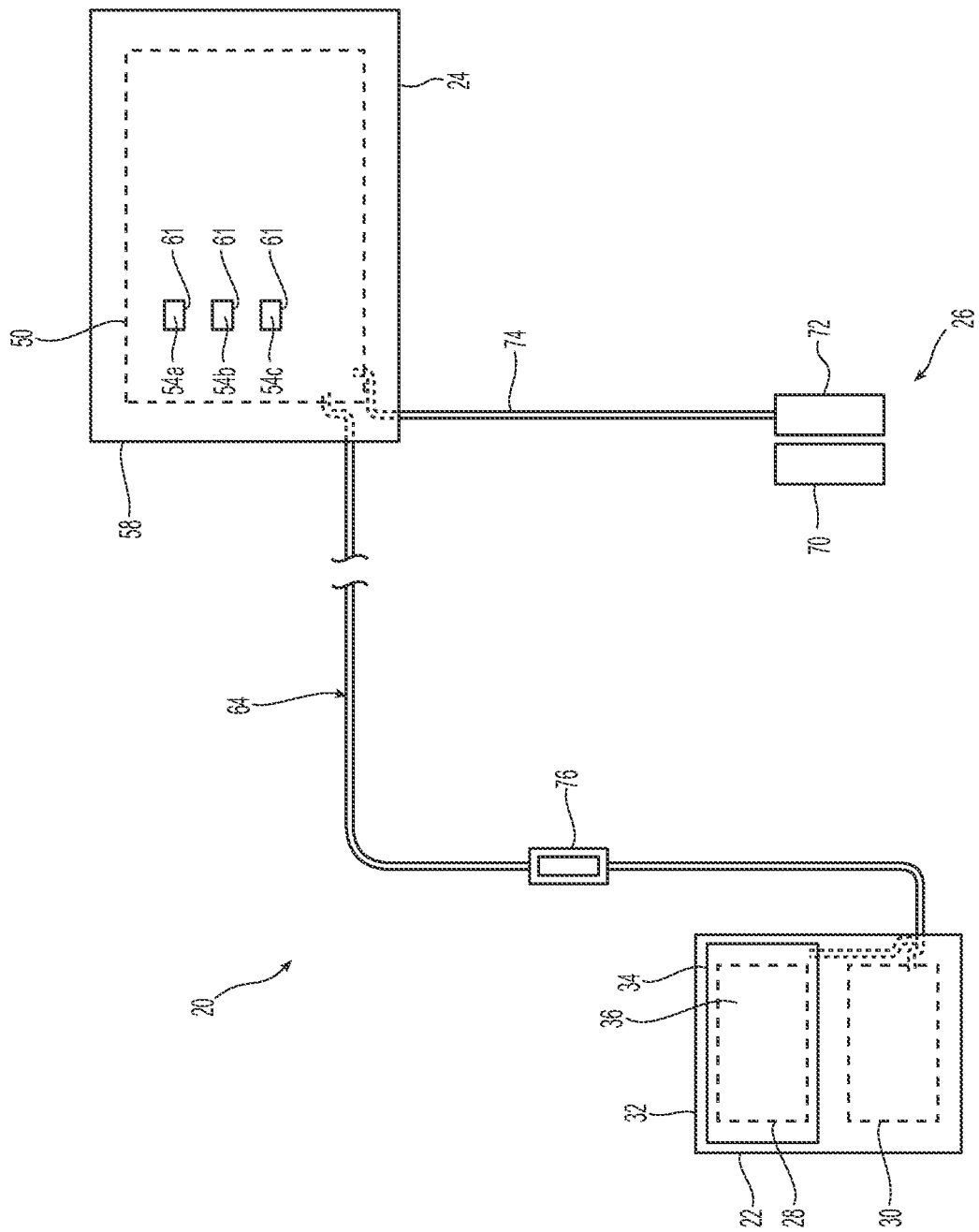
FIG. 2 is a schematic view of a patient monitoring system.
Figure 3:
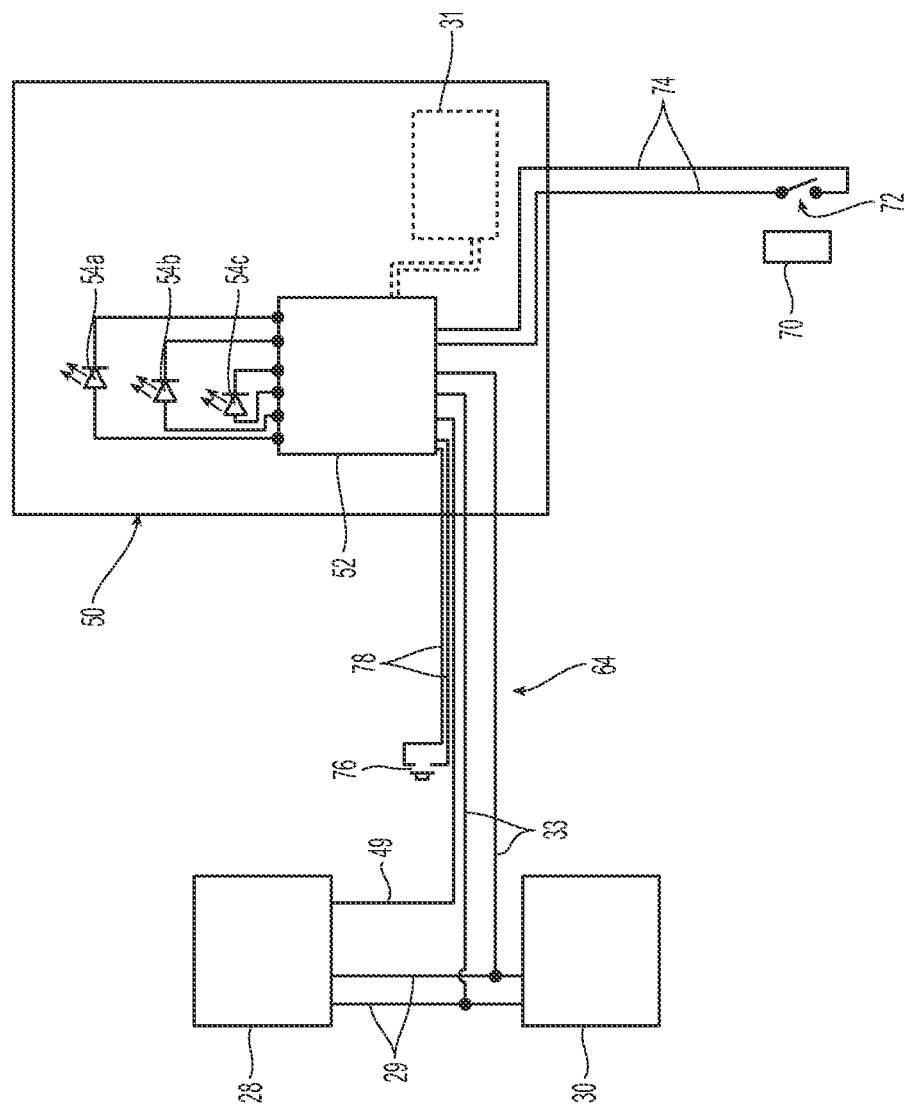
FIG. 3 is a diagrammatic view of a patient monitoring system.

Corresponding reference characters indicate corresponding parts throughout the several views. Although the exemplification set out herein illustrates an embodiment of the invention, in one form, the embodiment disclosed below is not intended to be exhaustive or to be construed as limiting the scope of the invention to the precise form disclosed.

DETAILED DESCRIPTION OF THE INVENTION

A patient monitoring system 20 is shown in FIG. 1 and includes a motion detection unit 22 and a control unit 24.

System 20 also includes a door sensor assembly 26 which is operably coupled with control unit 24. Motion detection unit 22 includes a motion detection sensor 28 and a removable power source 30. Motion detection sensor 28 may take the form of a passive infrared (PIR) motion detection sensor, range-controlled radar (RCR), a combination of PR and RCR technologies or other suitable motion detection technology. Motion detection sensors employing such detection methods are commercially available. For example, a GE 45132 Choice Alert Wireless Motion Sensor commercially available from General Electric Company can be modified for use in system 20. Removable power source 30 provides the electrical power necessary to operate motion detection sensor 28 and may take the form of one or more batteries. For example, power source 30 may take the form of a nine volt battery operably coupled with sensor 28 by conductive members 29.

A first housing 32 supports both the motion detection sensor 28 and power source 30. The illustrated housing 32 allows motion detection unit 22 to be easily mounted on a wall and also includes an opening 34 for motion detection sensor 28. A cover sheet 36 which does not interfere with the operation of motion detection sensor 28 covers opening 34. As best understood with reference to FIGS. 4 and 7, the illustrated housing 32 has a back plate 38 and a front piece 40. Backplate 38 includes a keyhole opening 42 which allows housing 32 to be supported on a fastener 44 extending from the wall. System 20 may also be provided with a mounting bracket having a ball joint or other adjustable mechanism for attaching housing 32 to the wall. The ball joint allows the orientation of sensor unit 22 to be easily adjusted. Such mounting brackets are commonly used with security system sensors and are commercially available.

FIG. 7 schematically depicts one manner in which back plate 38 and front piece 40 can be secured together. As shown, an inwardly projecting lip 46 on backplate 38 is engageable with a resilient latching member 48 to snap fit the two housing parts 38, 40 together. To detach the housing parts 38, 40, front piece 40 is pressed inwardly at each location of a latching member 48 to disengage the latching members 48 from lip 46.

Although one embodiment of housing 32 for the motion detection unit 22 is shown in the drawings, various alternative embodiments of the housing may also be employed. For example, alternative mounting methods may be used instead of keyhole 42 and fastener 44. Moreover, instead of employing two separable housing parts 38, 40, two parts hinged together could be employed, or, a single housing member having a battery compartment with a removable cover plate. As a person having ordinary skill in the art will recognize, still other housing configurations may also be used with motion detection unit 22.

Control unit 24 includes a printed circuit board 50 having control circuitry 52 and at least one light source 54a-54c operably coupled with circuitry 52. Advantageously, the light source is a light emitting diode (LED) mounted on printed circuit board 50. The illustrated embodiment includes three LEDs 54a-54c mounted on printed circuit board. Printed circuit board 50 also includes digital memory 56 for storing software instructions which govern the operation of system 20. Control unit 24 may optionally include a removable power source 31, e.g., four AA batteries.

A second housing 58 supports printed circuit board 50, LEDs 54a-54c mounted on printed circuit board 50 and optional power source 31. The illustrated housing 58 includes a front piece 60 and a backplate 62. Front piece 60 includes openings 61 for LEDs 54a-54c and is detachably securable to backplate 62 using latches engageable with a lip as depicted in FIG. 7 and described above with reference to first housing 32. Backplate 62 includes keyhole openings 42 for engagement with fasteners 44 whereby housing 58 is securable to a wall surface.

Electrically conductive wiring 64 extends between the first and second housings 32, 58 and operably couples motion detection sensor 28 with control circuitry 52. Wiring 64 includes at least one wire 49 communicating control signals between circuitry and sensor 28. Wiring 64 may also include wires 33 communicating electrical current from a removable power source located in one of the housings 32, 58 to the other housing whereby batteries located in either the first housing 32 or the second housing 58 may be used to power the entire system 20. If each of the units 22, 24 are provided with their own power source, wires 33 can be omitted.

If system 20 is entirely powered by a removable power source located in only one of the housings 32, 58, it will generally be advantageous to position the power source in the motion detection unit because the detection unit consumes more power than the control unit. Alternatively, a removable power source can be positioned in both housings or system 20 could be supplied with DC electrical power with an AC/DC adaptor connectable to a conventional electrical power outlet. System 20 could also be provided with connections for both batteries and an AC/DC adaptor whereby system 20 could be powered by either batteries or a conventional power outlet.

System 20 also includes a door sensor assembly 26 which detects whether door 68 is in an open or closed condition. In the illustrated embodiment, door sensor assembly 26 includes a permanent magnet 70 mounted on door 68 and a magnetic reed switch 72. Reed switch 72 is mounted adjacent the door opening so that magnet 70 will be positioned proximate reed switch 72 when the door is closed. The depicted reed switch 72 has a conventional design which, in the absence of a magnetic field, will be in an open position. Thus, when magnet 70 is positioned at a distance from switch 72 due to door 68 being in an open condition, switch 72 will be open. When magnet 70 is positioned proximate switch 72 by closure of door 68, magnet 70 will cause reed switch 72 to close. Magnetic reed switch 72 is operably coupled with printed circuit board 50 and control circuitry 52 via wiring 74. Reed switches provide a reliable and inexpensive sensor assembly which can be used to detect whether door 68 is open or closed, however, other sensing assemblies which are capable of determining whether door 68 is open or closed may also be used with system 20.

System 20 may also include an optional manual override switch 76. Switch 76 is operably coupled with printed circuit board 50 and control circuitry 52 with wires 78 forming a part of wiring 64. Switch 76 may take the form of a push button switch, however, other types of user-input devices may also be employed. As further discussed below, when switch 76 is pressed, it will temporarily suspend normal operation of system 20. This will allow a caregiver to enter the room and interact with the patient without causing system 20 to go into an alarm status. After a predetermined time period has elapsed or other preconditions satisfied following the activation of switch 76, system 20 will return to normal operation.

It is noted that, in the illustrated system 20, override switch 76 and reed switch 72 are separate from the first and second housings 32, 58. This provides greater flexibility in the mounting of system 20. Alternative embodiments of system 20, however, may include an override switch 76 and/or a reed switch 72 that is mounted within the housing of either of the motion detection unit 22 or control unit 24. In this regard it is noted that override switch 76 can be more easily integrated into detection unit 22 or control unit 24 than reed switch 72 which must be positioned closely adjacent door 68.

As can be readily understood with reference to FIGS. 4, 5 and 7, housings 32, 58 are mounted on a wall surface 80 with wiring 64 extending between housings 32, 58. Openings are provided in the side of housings 32, 58 to allow for the entry of wiring 64 which is routed through doorway 82 and exposed, i.e., mounted exterior to wall surfaces 80 instead of being routed within the wall structure. In the illustrated embodiment, it is only the mechanical fasteners used to mount system 20 to the walls which penetrate the wall structure and all of the electrical communicating components of system 20 are mounted exterior to wall surfaces 80.

If desired, a decorative or protective sleeve or cover can be positioned over wiring 64 on the outer surface of the walls. As used herein, wiring 64 provided with such a covering would still be considered exposed so long as it was positioned exterior to wall surfaces 80 and not routed through the interior of the wall. Mounting wiring 64 on a wall in an exposed manner and routing wiring 64 through doorway 82 provides significant cost savings during the installation of system 20. Healthcare facilities often have a large number of utilities routed within the wall structures partitioning individual rooms. If a newly installed piece of equipment requires a power or data line to be routed through the interior of a wall structure, there is often a bureaucratic procedure that must be followed to prevent the installation of the new power and data lines from interfering with infrastructure already present in the wall. Such processes greatly increase the costs of installing such equipment. System 20 avoids such costs by being installable on the exterior of the walls. While such cost savings will be present in new construction, this cost savings is particularly pronounced when retrofitting an existing healthcare facility structure. It would also be possible to route wiring 64 through the wall, however, wiring 64 is a flexible cable having a plurality of wires and is intended to be routed through doorway 82.

This mounting of system 20 also has other benefits. It allows for the temporary installation of a system 20 in a patient room. For example, for a room in a ward which typically treats patients who do not present fall risks. It also allows for the relatively easy repositioning of the system components. For example, if the interior of the room is repositioned and the bed repositioned, it may be necessary or beneficial to reposition motion detection unit 22. The use of a repositionable wall mounted unit, e.g., unit 22, instead of a permanently fixed unit allows system 20 to be easily adapted to the new room configuration.

The operation of system 20 will now be discussed. Motion detection unit 22 is mounted within the patient room 83 with motion detection sensor 28 oriented to detect movement in a detection zone 84 located above bed 86 whereby when patient 88 sits up sensor 28 will detect such movement. As best understood with reference to FIG. 8, patient 88 is located on a support surface 90 provided by bed 86 in the illustrated example. The lower boundary 92 of detection zone 84 is at least about 18 inches (45.7 cm) above support surface 90 in the area where patient 88 is located. In FIG. 8, dimension 94 is 18 inches and line 96 is 18 inches above support surface 90. By positioning the lower boundary 85 of detection zone 84 at least about 18 inches above support surface 90, patient 88 can roll-over and otherwise reposition themselves in a prone position on bed 86 without being detected by motion sensor 28. If, however, patient 88 sits upright they will move into detection zone 84 and trigger an alarm. By positioning the lower boundary 85 of detection zone 84 at least about 18 above support surface 90, the number of false alarms, i.e., detected motion which is not indicative of the patient attempting to exit bed 86, can be reduced while still detecting motion which is indicative of patient 88 attempting to exit bed 86. In this regard, it is noted that if patient 88 is going to attempt to get out of bed 86, they will typically first sit upright with their upper torso projecting into detection zone 84 and extend their feet toward the floor. Thus, the area between dotted lines 98 above the patient's upper torso is the detection area of most concern and having lower boundary 92 positioned closely proximate a line 96 which is 18 inches above support surface 90 will generally detect motion if patient 88 exits but still allow patient 88 to reposition themselves on bed 86 without triggering a false alarm. Motion detection sensor 28 has a generally conical detection zone 84. The shape of detection zone 84, however, can be modified by the use of blinders or a shaped opening in housing 32. For example, an alternative embodiment of detection unit 22 could have a 32 with repositionable blinders which alter the dimensions of opening 34 whereby the boundaries of detection zone 84 could be adjusted.

An alternative placement of the motion detection unit is also depicted in dashed lines in FIGS. 1 and 8. In FIGS. 1 and 8, unit 22a depicts the placement of a motion detection unit relatively close to the floor. When mounted in this lowered position, the motion detection unit 22a has a detection zone 84a with a lower boundary 92a that intersects the floor surface relatively close to the unit 22a. The lower boundary 92a corresponds to the floor surface once it has intersected the floor. Unit 22a is positioned below the support surface 90 such that upper boundary 93a is below support surface 90 when it impinges upon bed 86 whereby the detection zone 84a does not include any space directly above support surface 90. When using a low mounted unit 22a, it will generally be desirable for upper boundary 93a of detection zone 84a to be no higher than support surface 90 proximate support surface 90 for the entire extent of support surface 90 as depicted in FIG. 8.

By mounting detection unit 22a below support surface 90, movement of the patient in the space above support surface 90, e.g., sitting up or rolling over, will not be detected by unit 22a or generate an alarm signal. When the patient 88 removes their feet from the bed to position them on the floor, however, their feet will intersect detection zone 84a and generate an alarm signal. It is noted that some hospital beds do not include a clear space adjacent the floor which would allow detection zone 84a to extend under and to all sides of the bed. In such situations, a second unit mounted below support surface 90 could be employed to provide the coverage desired. Alternatively, a unit 22 mounted above the support zone 90 could be used. In still other circumstances, it may be desirable to utilize motion detection units 22 that are mounted both above and below support surface 90.

Control unit 24 is mounted in hallway 83 on the opposite side of doorway 82 from sensor unit 22 with door sensor assembly 26 being mounted on and proximate door 68. Wiring 64 is routed through doorway 82 to operably couple sensor unit 22 with control unit 24.

In the illustrated embodiment, control unit 24 includes three LEDs 54a-54c but does not include any audible alarms. The absence of an audible alarm allows system 20 to be installed in a healthcare facility without increasing the noise level of the facility. Various different means may be used to signal an alarm event and current status of system 20. In the illustrated embodiment, LED 54a is a green light and illumination of LED 54a indicates that system 20 is active and no movement has been detected. LED 54b is a red light and illumination of LED 54b indicates that motion has been detected. LED 54c is an amber light and illumination of LED 54c indicates that system 20 is inactive. In operation, system 20 will typically be used with fall-risk patients and illumination of LED 54*b* will alert caregivers that the patient is attempting to leave the bed and that a caregiver should check on the patient to provide assistance and limit the potential for an injury-causing fall.

Control circuitry 52 is configured to illuminate LED 54*b* when motion detector 28 senses movement and door sensor assembly 26 detects that door 68 is closed. LED 54*b* may be kept illuminated only during the time period during which such movement is detected, or, it may remain illuminated for a predetermined time period, e.g., 5 or 10 minutes, after detecting motion with door 68 in a closed condition. Alternatively, LED 54*b* may be kept illuminated until door 68 is opened. Still another option is to keep LED 54*b* illuminated until both the expiration of a predetermined time period and the opening of door 68 occurs. If system 20 includes an override switch 76, another option is to retain LED 54*b* in an illuminated condition until override switch 76 is activated.

As mentioned above, the purpose of illuminating LED 54*b* is to alert a caregiver that patient 88 has moved and may be exiting bed 86. The preferred method of terminating the alert provided by LED 54*b* may depend, in part, on the physical layout, staffing and procedures of the healthcare facility in which system 20 is installed.

As mentioned above, control circuitry 52 illuminates LED 54*a* when system 20 is active and door 68 is in a closed condition and motion sensor 28 has not detected movement. If door 68 is opened, control circuitry 52 will illuminate LED 54*c* to indicate that system 20 is inactive and will also prevent the illumination of LED 54*b*. This will allow a caregiver to enter the room leaving door 68 in an open condition, attend to patient 88, and then leave the room closing the door, without causing system 20 to go into an alarm condition, i.e., illuminate LED 54*b*, while the caregiver is in the room attending to patient 88.

While many tasks required of a caregiver can be performed with door 68 in an open condition and without privacy concerns, it will be preferable to close door 68 for some caretaker tasks for reasons of patient privacy. System 20 may optionally include an override switch 76 for such situations. If an override switch 76 is provided, the caregiver can enter the room, activate switch 76, close door 68 and then attend to the care of patient 88 without causing an alarm condition. Activation of switch 76 will cause system 20 to illuminate LED 54*c* and prevent the illumination of LED 54*b* until certain preconditions have been met or a predetermined time period has elapsed even though movement is being detected by sensor 28 and door 68 is closed.

System 20 can be provided with a switch 76 on either side of door 68. When switch 76 is located on the same side of door 68 as motion detection unit 22, activation of switch 76 advantageously places system 20 in an inactive condition until door 68 is opened and once again closed indicative of the care giver leaving the room. As previously mentioned, an alternative approach would be for activation of switch 76 to place system 20 in an inactive condition for a predetermined period of time, e.g., five or ten minutes. Various other embodiments of system 20 could utilize other preconditions for determining when to return system 20 to normal operation.

While the illustrated embodiment includes three LEDs 54*a*-54*c*, alternative embodiments of system 20 may utilize control units having a different number of light sources. For example, LED 54*c* could be omitted from system 20 and the absence of any lighted LED on the control unit would be used to indicate that system 20 was in an inactive state. Alternatively, if only two lights were provided, it could be LED 54*a* that is omitted with the absence of any illuminated light indicating that the system is operating and is not detecting movement. Still other variations of illuminated elements could be employed to communicate the status of the system.

With regard to such variations, it is noted that the embodiment described above includes an LED 54*b* that has an alarm condition which indicates that the door is closed and motion is detected and a non-alarm condition which are indicated by selective illumination of LED 54*b*. In the described embodiment, the alarm condition is indicated by illumination of LED 54*b* and the non-alarm condition is indicated by the non-illumination of LED 54*b*. It will generally be desirable to indicate the alarm condition by illumination of LED 54*b*, however, it would be possible to indicate the alarm condition by non-illumination and the non-alarm condition. It would also be possible for a single LED light to indicate multiple non-alarm conditions. For example, continuous illumination of a light could indicate an alarm condition, non-illumination of the same light could indicate that the system was operating normally without detecting patient movement and slow blinking of the light could indicate that the battery was low or that the system had been temporarily suspended from normal operation by activation of the override switch.

As can be understood from the foregoing discussion, system 20 is well-adapted for use in health-care facilities having a closed door policy wherein the doors of patient rooms are kept closed unless another person is present in the room with the patient. Such policies are generally intended to shield patients from excessive noise and the lack of an audible alarm on system 20 also facilitates the operation of such care facilities. In this regard it is noted that LED 54*b* is the sole alarm or alert communication element of system 20. Alternative embodiments of system 20, however, could include wireless transmitter to communicate alarms and other status information to a central base unit. For example, wireless base units which are designed for communication with multiple motion sensor units similar to units 22 are commercially available from General Electric Company. The wireless communications may be transmitted using ZigBee or other suitable protocols.

While this invention has been described as having an exemplary design, the present invention may be further modified within the spirit and scope of this disclosure. This application is therefore intended to cover any variations, uses, or adaptations of the invention using its general principles.

What is claimed is:

1. A patient monitoring system for use proximate a doorway with a door, the system comprising:
   a motion detection unit including a motion detection sensor and a first housing supporting the motion detection sensor;
   a control unit including control circuitry, at least one light operably coupled with the control circuitry and a second housing supporting the control circuitry and the light, the light indicating one of an alarm condition and a non-alarm condition by selective illumination of the light;
   wiring extending between the first housing and the second housing and operably coupling the motion detection sensor with the control circuitry wherein the control circuitry receives signals from the motion detection sensor;
   a door sensor assembly securable proximate a door, the door sensor assembly being operably coupled with the control circuit and thereby communicating the open/closed status of the door to the control circuitry; and wherein the control circuitry is configured to place the light in the alarm condition when the motion detector senses movement and the door sensor assembly detects that the door is closed.

2. The system of claim 1 wherein each of the first and second housings are configured to support a removable power source and conductively couple the power sources with the system.

3. The system of claim 1 wherein one of the first and second housings in configured to support a removable power source and conductively couple the power source with the system and wherein the removable power source is the sole source of electrical power for the system with electrical current from the removable power source being communicated between the first and second housings by the wiring.

4. The system of claim 1 wherein the control circuitry places the light in the non-alarm condition when the motion detector senses movement and the door sensor assembly detects that the door is open.

5. The system of claim 1 wherein the door sensor assembly includes a magnet mountable on the door and a magnetic reed switch operably coupled with the control circuitry and mountable proximate the door whereby closing the door positions the magnet proximate the reed switch and opening the door separates the magnet from the reed switch.

6. The system of claim 5 wherein second wiring operably couples the reed switch to the control unit.

7. The system of claim 1 further comprising a manual override switch wherein activation of the override switch prevents the light from entering the alarm condition when the motion detector detects motion and the door sensor assembly detects that the door is closed.

8. The system of claim 7 wherein activation of the manual override switch prevents the light from entering the alarm condition for a predetermined period of time and wherein following the predetermined period of time, the light is placed in the alarm condition when the motion detector senses movement and the door sensor assembly detects that the door is closed.

9. The system of claim 1 wherein the control circuitry is disposed on a printed circuit board and the light is an LED light mounted on the printed circuit board.

10. The system of claim 1 wherein the first and second housings are each adapted for mounting on a wall surface with the wiring extending therebetween being exposed on the wall surface.

11. The system of claim 1 wherein the status of the at least one light is the sole alert communication element of the system.

12. Method of installing a patient monitoring system:
attaching a first housing to a first wall surface on a first side of a door opening, the first housing supporting a motion detection sensor;
attaching a second housing to a second wall surface on an opposite side of the door opening, the second housing supporting control circuitry and at least one light operably coupled with the control circuitry, the light indicating one of an alarm status and a non-alarm status by selective illumination of the light;
operably coupling the motion detection sensor with the control circuitry by extending wiring therebetween with the wiring extending through the door opening;
mounting a door sensor assembly proximate the door opening and operably coupling the door sensor assembly with the control circuitry;
detecting whether the door is open or closed with the door sensor assembly; and
placing the light in the alarm condition when the motion detector senses movement and the door sensor assembly detects that the door is closed.

13. The method of claim 12 further comprising preventing the light from entering the alarm condition when the motion detector senses movement and the door sensor assembly detects that the door is open.

14. The method of claim 12 further comprising the step of providing a manual override switch wherein activation of the override switch prevents the light from entering the alarm condition when the motion detector detects motion and the door sensor assembly detects that the door is closed.

15. The method of claim 14 wherein activation of the manual override switch prevents the light from entering the alarm condition for a predetermined period of time and wherein following the predetermined period of time, the light is placed in the alarm condition when the motion detector senses movement and the door sensor assembly detects that the door is closed.

16. The method of claim 12 wherein the status of the at least one light is the sole alert communication element of the system.

17. The method of claim 12 further comprising the provision of a removeable power source supported by one of the first and second housings, the removeable power source being the sole source of electrical power for the system with electrical current from the removable power source being communicated between the first and second housings by the wiring.

18. The method of claim 12 wherein all electrical communicating components of the system are mounted exterior to the first and second wall surfaces.

19. The method of claim 12 wherein the system monitors a patient located on a support surface, the method further comprising positioning the first housing on the first wall surface wherein the motion detection sensor defines a detection zone having a lower boundary which is at least about 18 inches above the support surface.

20. The method of claim 12 wherein the system monitors a patient located on a support surface, the method further comprising positioning the first housing on the first wall surface below the support surface wherein the motion detection sensor defines a detection zone that is proximate the support surface but does not extend directly above the support surface.

* * * * *